United States Patent [19]

Ritter et al.

[11] 4,237,892
[45] Dec. 9, 1980

[54] MULTI-BEVELED, V-SHAPED NEEDLE POINT

[75] Inventors: Thomas A. Ritter, New Fairfield; Leonard J. Laskowski, Middletown; Donald S. Kaplan, Ridgefield, all of Conn.

[73] Assignee: American Cyanamid Company, Stamford, Conn.

[21] Appl. No.: 12,686

[22] Filed: Feb. 16, 1979

[51] Int. Cl.³ .............................................. A61B 17/06
[52] U.S. Cl. .................................................... 128/339
[58] Field of Search ................................ 128/221, 339

[56] References Cited

U.S. PATENT DOCUMENTS

| 2,092,929 | 9/1937 | Ovington | 128/339 |
| 2,560,162 | 7/1951 | Ferguson | 128/221 |
| 2,841,150 | 6/1958 | Riall | 128/339 |
| 3,038,475 | 6/1962 | Orcutt | 128/339 |
| 3,094,123 | 7/1963 | Kurtz | 128/339 |
| 3,265,070 | 8/1966 | Kurtz | 128/339 |
| 3,955,558 | 5/1976 | Ruisz | 128/221 |
| 4,128,351 | 12/1978 | Kurtz et al. | 128/339 |

Primary Examiner—Robert W. Michell
Assistant Examiner—C. W. Shedd
Attorney, Agent, or Firm—Jack W. Richards

[57] ABSTRACT

This invention relates to a surgical needle comprising a point and dual cutting blades. The point is defined by a symmetrical angle of width and an angle of slope. The needle point geometry and the dual cutting blades provide a flap incision and a reduction in the tissue penetration properties.

7 Claims, 7 Drawing Figures

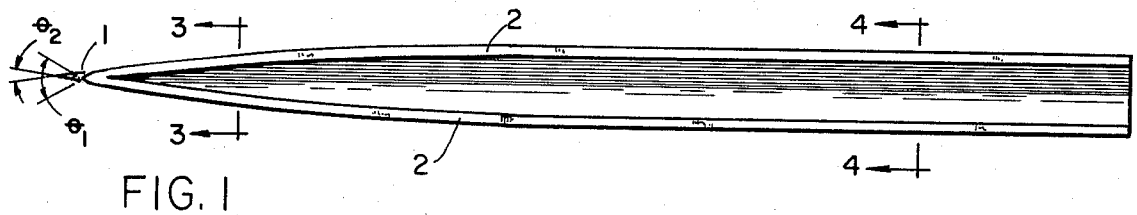
FIG. 1
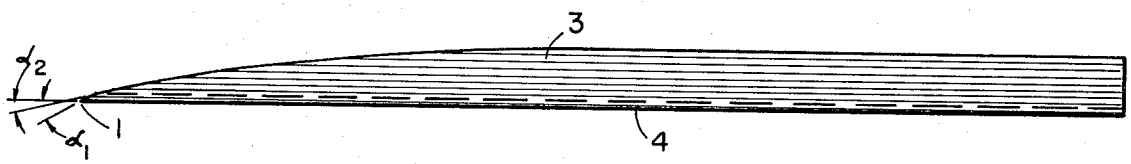
FIG. 2
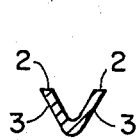
FIG. 3
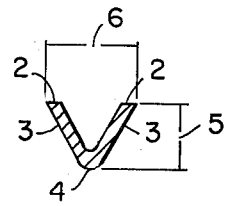
FIG. 4
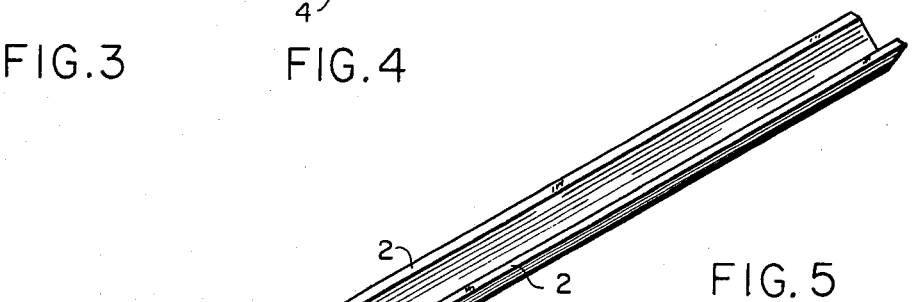
FIG. 5
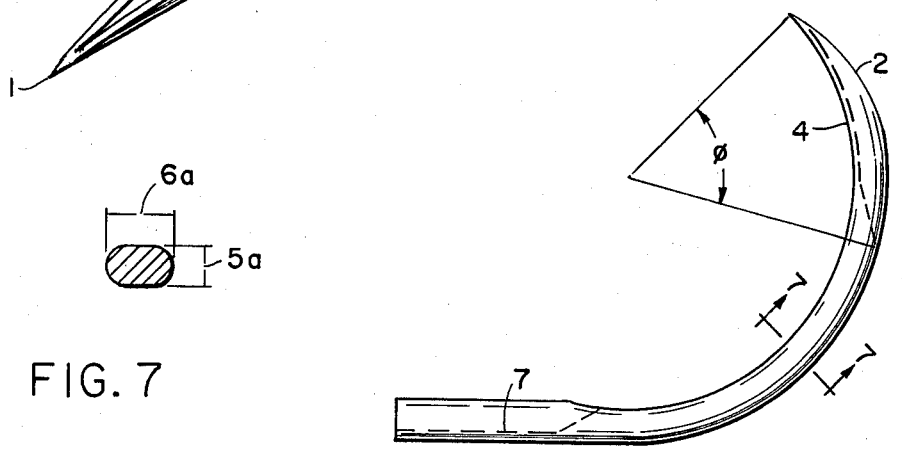
FIG. 7
FIG. 6

MULTI-BEVELED, V-SHAPED NEEDLE POINT

BACKGROUND AND SUMMARY OF THE INVENTION

This invention relates to a surgical needle comprising a point and dual cutting blades. The point is defined by a symmetrical angle of width and an angle of slope. The needle point geometry and the dual cutting blades provide a flap incision and a reduction in the tissue penetration properties.

The Applicants are not aware of any prior art which, in their respective judgements as persons skilled in the art of surgical needle of this invention. However, to fully develop the background of the invention and establish the state of the art, the following references are cited:

U.S. Pat. No. 3,094,123 issued June 18, 1963 which discloses a surgical needle having an angle of slope and an angle of sharpness and providing a reduction in tissue penetration force; and U.S. Pat. No. 2,841,150 issued July 1, 1958 which discloses a surgical needle having a triangular cross-section. Both of these patents are incorporated by reference.

The surgical needle of this invention has advantages over the references above. The needle point geometry and the V-shape cross-section provide a reduction in the tissue penetration force and a flap incision, rather than a circular, eliptical or triangular incision of the prior art needles. The advantage of the flap incision is that the flap formed can then close over the puncture defect. This may accelerate the physiological healing of the puncture defect. The flap may also reduce fluid leakage from soft tissue. Another advantage is the dual cutting blades which can provide up to four cutting edges.

Still another advantage is that the V-shape cross-section of the needle is based on a structural beam concept (which is described in U.S. Pat. No. 2,841,150). The thickness of the needle sides can thus be reduced while providing sufficient rigidity to penetrate tissue. Alternatively, the needle height and width can be decreased which reduces the tissue penetration force.

The needle of this invention is useful as a cutting edge or a taper point surgical needle. The needle is used in the same manner as a conventional cutting edge or taper point needle.

A surgical needle providing a reduction in the tissue penetration force and a flap incision has now been invented. A straight or curved needle is within the scope of the invention. The needle comprises a penetration portion, a middle portion and a butt portion. The penetration portion initiates at a point. The point is defined by a symmetrical angle of width and an angle of slope. The penetration portion terminates in dual cutting blades having a V-shape cross-section. The cutting blades are joined at the apex of the V-shape. The butt portion of the needle has strand attachment means.

In a preferred embodiment, the point is defined by a symmetrical angle of width of about 20° to 35°. In another preferred embodiment, the point is defined by an angle of slope of about 20° to 35°. In other preferred embodiments, the sides of the V-shape cross-section have an included angle of about 60°; and, the middle portion has a cross-section as described in FIG. 7 below or a V-shape cross-section.

BRIEF DESCRIPTION OF THE DRAWINGS

FIGS. 1 and 2 are top and side views, respectively, of the penetration and middle portions of a straight needle of this invention;

FIG. 3 is a section view on the line 3—3 of FIG. 1 showing a cross-section of the penetration portion of the needle;

FIGS. 4 and 7 are section views on the lines 4—4 of FIG. 1 and 7—7 of FIG. 6 showing alternative cross-sections of the middle portion of the needle;

FIG. 5 is a projected view of FIGS. 1 and 2;

FIG. 6 is a side view of a curved needle of this invention.

DESCRIPTION OF THE PREFERRED EMBODIMENT

FIGS. 1 and 2 describe the penetration and middle portions of a straight surgical needle of this invention. The needle initiates at a point 1 and terminates in dual cutting blades 2. The sides 3 of the penetration portion have a V-shape cross-section (shown in FIG. 3) and are jointed at the apex 4 of the V-shape. The point geometry of the needle of this invention reduces the force necessary to penetrate tissue. The point 1 is defined by a symmetrical angle of width and an angle of slope. In a preferred embodiment, the point 1 is defined by a symmetrical primary and secondary angle of width, $\theta_1$ and $\theta_2$, respectively; and by a primary and secondary angle of slope, $\alpha_1$ and $\alpha_2$, respectively. The preferred angle for $\theta_1$ is about 20° to 35° and for $\theta_2$ is about 5° to less than 20°; and for $\alpha_1$ is about 20° to 35° and for $\alpha_2$ is about 5° to 30° with the proviso that $\alpha_2$ is always less than $\alpha_1$. The most preferred angle for $\theta_1$ is about 30° and for $\theta_2$ is about 10°; and for $\alpha_1$ is about 25° and $\alpha_2$ is about 10°. The secondary angle of width $\theta_2$ is always less than the primary angle $\theta_1$; and the secondary angle of slope $\alpha_2$ is always less than the primary angle $\alpha_1$. Within the scope of this invention is a point, defined by primary and secondary angles of width and angles of slope, in which the tip is rounded or blunted, for example, by grinding.

FIG. 3 is a section view on the line 3—3 of FIG. 1 and describes the preferred V-shape cross-section of the penetration portion. FIG. 4 is a section view on the line 4—4 of FIG. 1 and describes a cross-section of the middle portion of the needle. An alternative cross-section is described in FIG. 7. The width of the cutting edges 2 and the thickness of the sides 3 are constant. The height and width of the sides 3 of the penetration portion increase away for the needle point to a maximum height 5 and maximum width 6 of the middle portion shown in FIG. 4. The maximum height 5 and width 6 is less than or equal to the maximum height and width of the penetration portion. The maximum height 5 of the needle is dependent on the type of surgical operation or procedure. The following types of surgical operations or procedures and the range of the maximum height 5 are examples: ophthalmic—about 0.006 to 0.011 inches; thoracic—about 0.011 to 0.022 inches; plastic or reconstructive—about 0.013 to 0.017 inches; general—about 0.022 to 0.050 inches (and larger for special applications); and retention suturing—up to about 0.062 inches. Using these ranges with the included point angle and needle point geometry, the remaining dimensions of the needle can be determined. The included angle of the sides 3 in the penetration and middle portions of the needle is constant. In the preferred embodiment, the included angle is about 60°. The apex 4 of the sides 3 can be rounded as shown in FIG. 4.

FIG. 5 describes a projected view of the penetration and middle portions of a straight surgical needle described in FIGS. 1 and 2. The butt portion of a straight needle described in FIGS. 1, 2 and 5 contains a strand attachment means, for example, a channel 7 described in FIG. 6, or a drilled end.

FIG. 6 describes a side view of a curved needle of this invention. The length of the V-shape cross-section of the penetration portion is defined by an included point angle, $\phi$ which for illustration only is shown as about 60°. It is to be understood that an included point angle of $\phi$ below 60° is within the scope of this invention. As a maximum, the included point angle, $\phi$ can be the arc circumscribed by the needle of FIG. 6; that is, the entire cross-section of the needle of FIG. 6 can be V-shape.

In FIG. 6, the apex 4 is shown on the inside radius and the dual cutting edges 2 are shown on the outside radius of the needle. However, it is within the scope of this invention to have the apex on the outside radius and the dual cutting edges on the inside radius of the needle. The middle portion of the needle is defined by the remaining curved portion of the needle in FIG. 6. The butt portion of the needle, which may also be curved, contains a strand attachment means, for example, a channel 7 or a drilled end.

FIG. 7 is a section view on the line 7—7 of FIG. 6 and describes a cross-section of the middle portion. An alternative cross-section is described in FIG. 4. The middle portion of a straight or curved needle of this invention can also have a solid elliptical, triangular or circular cross-section. Generally, the configuration of the middle portion is not critical provided that the maximum height and width of the middle portion is less than or equal to the maximum height and width of the penetration portion. The maximum height 5a and width 6a is less than or equal to the maximum height and width of the penetration portion.

In the manufacture of needles having a V-shape cross-section throughout, preformed sheet stock is used. The needles, either straight or curved, are manufactured by conventional techniques, e.g., as generally described in U.S. Pat. No. 2,841,150. In the manufacture of needles where only the penetration portion has a V-shape cross-section, the needles are cut from stock having a solid cross-section. The V-shape is then formed by a stamping or swaging operation. The needles are then manufactured by conventional techniques. The honing of the symmetrical angle of width and the angle of slope, and the sharpening of the dual cutting edges is then accomplished, for example, by machine grinding. The grinding machines and grinding techniques used are conventional.

The needle can be manufactured from any known surgical suture needle material, for example, steel or a nonferrous alloy. Other materials, such as polymers, or composite polymer/metal materials may also be used.

I claim:

1. A surgical needle comprising a penetration portion initiating at a point defined by a symmetrical primary angle of width of about 20° to 35° and a secondary angle of width of about 5° to less than 20° and a primary angle of slope of about 20° to 35° and a secondary angle of slope of about 5° to 30°, with the proviso that the secondary angle of slope is always less than the primary angle of slope, and terminating in dual cutting blades providing four cutting edges and having a V-shaped cross-section and joined at the apex of said V-shape; a middle portion; and a butt portion having strand attachment means.

2. A needle of claim 1 wherein the primary angle of idth is about 30° and the secondary angle of width is about 10°.

3. A needle of claim 1 wherein the primary angle of slope is about 25° and the secondary angle of slope is about 10°.

4. A needle of claim 1 wherein the sides of the V-shaped cross-section has an included angle of about 60°.

5. A needle of claim 1 wherein the middle portion has a generally elliptical cross-section which is flattened on opposite sides; said sides being substantially parallel to each other and to the major axis of the generally elliptical cross-section; said axis being substantially parallel to a line which connects the two outermost cutting edges of said V-shaped cross-section.

6. A needle of claim 1 wherein the middle portion has a V-shape cross-section.

7. A needle of claim 1 wherein the penetration and middle portion are curved.

* * * * *